United States Patent [19]

Cavazza

[11] Patent Number: 5,430,065
[45] Date of Patent: Jul. 4, 1995

[54] THERAPEUTICAL METHOD FOR ENHANCING PERIPHERAL GLUCOSE UTILIZATION IN A NON-INSULIN-DEPENDENT DIABETIC PATIENT

[75] Inventor: Claudio Cavazza, Rome, Italy

[73] Assignee: Sigma-Tau Industrie Farmaceutiche Riunite S.P.A., Rome, Italy

[21] Appl. No.: 132,817

[22] Filed: Oct. 7, 1993

[30] Foreign Application Priority Data

Oct. 8, 1992 [IT] Italy .................. RM92A0731

[51] Int. Cl.6 ............ A61K 31/22; A61K 31/205
[52] U.S. Cl. ................... 514/556; 514/546; 514/547; 514/866; 426/801
[58] Field of Search ........... 514/23, 546, 547, 556, 514/866; 426/801

[56] References Cited

U.S. PATENT DOCUMENTS

| | | | |
|---|---|---|---|
| 4,194,006 | 3/1980 | Cavazza | 424/312 |
| 4,343,816 | 8/1982 | Cavazza | 424/316 |
| 4,346,107 | 8/1982 | Cavazza et al. | 424/316 |
| 4,415,588 | 11/1983 | Cavazza | 514/556 |
| 4,415,589 | 11/1983 | Cavazza | 514/556 |
| 4,464,393 | 8/1984 | Cavazza | 514/556 |
| 4,663,352 | 5/1987 | Onofrj | 514/556 |
| 4,751,242 | 6/1988 | Calvani et al. | 514/554 |
| 4,771,075 | 9/1988 | Cavazza | 514/556 |
| 4,921,877 | 5/1990 | Cashmere et al. | 514/866 |
| 5,037,851 | 8/1991 | Cavazza | 514/556 |
| 5,043,355 | 8/1991 | Cavazza | 514/547 |
| 5,070,074 | 12/1991 | Medina et al. | 514/866 |
| 5,145,871 | 9/1992 | Cavazza | 514/546 |
| 5,173,508 | 12/1992 | Cavazza | 514/547 |
| 5,192,805 | 3/1993 | Cavazza | 514/556 |
| 5,292,723 | 3/1994 | Audrey et al. | 514/23 |

*Primary Examiner*—Ronald W. Griffin
*Attorney, Agent, or Firm*—Oblon, Spivak, McClelland, Maier, & Neustadt

[57] ABSTRACT

A novel therapeutical use of L-carnitine, acyl L-carnitines and the pharmacologically acceptable salts thereof is disclosed for the treatment of non-insulin-dependent patients with a view to enhancing their peripheral glucose utilization.

3 Claims, No Drawings

THERAPEUTICAL METHOD FOR ENHANCING PERIPHERAL GLUCOSE UTILIZATION IN A NON-INSULIN-DEPENDENT DIABETIC PATIENT

The present invention relates to a new therapeutic use of L-carnitine, acyl L-carnitines wherein the acyl is a straight or branched-chain acyl group having 2-6 carbon atoms for the long-term treatment of non-insulin-dependent diabetic patients with a view of enhancing their peripheral glucose utilization.

Among the acyl L-carnitines the acyl group whereof has 2-6 carbon atoms, acetyl, propionyl, butyryl, valeryl and isovaleryl L-carnitine are particularly preferred. Pharmaceutically acceptable salts of L-carnitine include all pharmaceutically acceptable salts which are prepared by the addition of acid to L-carnitine, and which do not give rise to undesirable toxic or collateral effects. The formation of pharmaceutically acceptable acid addition salts is well known in pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

For the sake of simplicity and clarity, hereinbelow reference will be made to L-carnitine only, it being understood, however, that whatever disclosed in connection with L-carnitine equally applies to the above identified acyl L-carnitines and the pharmacologically acceptable salts thereof.

As is well known, diabetes mellitus is a syndrome resulting from the interaction of hereditary and environmental factors and characterized by abnormal insulin secretion and by various metabolic and vascular manifestations which express themselves as a tendency to develop high blood glucose levels, accelerated non-specific atherosclerosis, neuropathy and thickening of the capillary basal lamina causing deterioration of the kidneys and the retina.

The current classification of diabetes distinguishes primarily between the following two main categories: insulin-dependent (or type-I) diabetes, which affects patients who are literally dependent on exogenous insulin to prevent ketoacidosis and death; and non-insulin-dependent (or type-II) diabetes, which affects patients who are Free to use insulin or not as they please for relieving the symptoms of diabetes, but who do not strictly need to take insulin in order to survive.

As regards endogenous insulin secretion, patients suffering from type-I diabetes present insulin deficiency, whereas those with type-II diabetes present variable insulin levels (sometimes even above normal) with insulin resistance.

In particular, with regard to the now well-known use of L-carnitine in diabetes, this treatment is given to patients with type-I diabetes (i.e. insulin-deficient), the purpose of L-carnitine administration being to reduce the insulin dose necessary to achieve a given effect carbohydrate metabolism, thus permitting an insulin "saving".

This known use provides no suggestion or hint as to the possible efficacy of carnitine in the treatment of patients with type-II diabetes, who may have normal or above-normal serum insulin values.

1st CLINICAL TRIAL

Intravenous Administration

The trial was conducted to assess the effects of acute intravenous administration of L-carnitine on insulin-mediated glucose utilization in patients with non-insulin-dependent diabetes mellitus.

Nine non-insulin-dependent diabetics, aged from 39 to 64 years, were recruited into the trial. Their main clinical parameters are shown in the table.

Two patients were treated with insulin and seven with oral hypoglycaemic agents.

The patients were told to comply strictly with the therapeutic regimen and to consume an isocaloric diet containing 200 g of carbohydrates throughout the entire study period. Control of blood glucose levels was good in all patients, as shown by the fact that fasting plasma glucose levels and $HbA_{1c}$ were below 140 mg/dl and 8%, respectively.

Measurements were taken in the morning after overnight fasting. Polyethylene cannulas were inserted in an antecubital vein to administer the test substances and retrogradely in a vein of the hand for intermittent blood sample collection.

The hand was warmed in a heated container (60° C.) to allow arterialization of venous blood.

Each patient was studied twice, in random order, once with carnitine and the other time with saline solution. A minimum period of one week was allowed to elapse between the two observation sessions.

At the beginning of each session ($-120$ min), $3[^3H]$ glucose (Amersham Ltd., Buckinghamshire, U.K.) was infused in a 25 uCi bolus, followed by continuous infusion for 4 h. At $-60$ min a first-line-attack bolus of L-carnitine (3 mmol) or saline solution was administered, followed by continuous infusion of 1.7 umol/min for 3 h. At time 0 a normoglycaemic insulin clamp was used to assess the sensitivity to insulin [De Fronzo et al. (1979) Glucose clamp technique: a method for quantifying insulin secretion and resistance. Am. J. Physiol. 237, E214-223].

Peripheral plasma insulin concentrations were raised in acute treatment and maintained at 60 uU/ml by means of a constant infusion (0.8 mU/kg/min) of normal insulin. The plasma glucose concentration was allowed to drop from 140 to 100 mg/dl, a clamp being applied at this latter value by means of variable glucose infusion.

The glucose infusion rate was adjusted by measuring plasma glucose at 5 min intervals by means of a Beckman glucose analyzer.

The blood samples determinations of the hormone, substrate and specific glucose activity were taken at 10-30 min intervals.

Plasma glucose was measured using the glucose-oxidase method (with a Beckman analyzer). Plasma insulin was measured by RIA [Debuquois B.et al., G.d. (1971) Use of polyethylene glycol to separate free and antibody bound peptide hormones in radioimmunoassay. J. Clin. Endocrinol. Metab. 33, 732-738].

Blood lactate was measured on the perchloric extract of whole blood by means of the enzymatic procedure described by Gutman [Gutman I. et al. (1974) L-(+)-Lactate determination with lactate dehydrogenase and NAD. In: H. U. Bergmayer (Ed.), Methods of Enzymatic Analysis. Academic Press Inc., New York, pp.1464-1468].

Plasma free fatty acids were determined by means of the enzymatic method described by Noma A. et al. (1973) A new colorimetric microdetermination of free fatty acids in serum. Clin. Chim. Acta 43, 317–320.

The results of the study were as follows: in the postabsorption state, the plasma glucose concentration was similar in controls (142±8 mg/dl) and in patients treated with carnitine (140±7 mg/dl), and a clamp was performed at the same level (100 mg/dl) in both groups with a coefficient of variation below 5%. The time taken for blood glucose levels to drop From the baseline value to the normoglycaemic level was 46 and 54 min in controls and carnitine-treated subjects, respectively. Plasma insulin levels were 11±1 in controls and 9±1 uU/ml in carnitine-treated subjects and rose to a similar plateau of 60 uU/ml during insulin infusion. Despite the similar plasma insulin levels, the amount of glucose metabolized by tire entire body was significantly higher during carnitine infusion (4.05±0.37 mg/kg/min) than during infusion of saline solution (3.52±0.36; $P<0.05$).

In 6 patients out of 9, the increase in utilization of total glucose ranged from 10 to 50%. Lactate concentrations were similar in the two groups in the fasting state. In the control group blood lactate remained substantially unchanged. In contrast, carnitine infusion caused a marked reduction in lactate concentration from baseline ranging from 25 to 40% ($P<0.05$–0.005). Plasma free fatty acid levels were similar in the basal state in the two groups with mean values of 0.48±0.05 mmol/l (in controls) and 0.62±0.12 mmol/l (in subjects treated with carnitine) and were reduced to similar extents (0.1 mmol/l) during insulin infusion. Production of endogenous glucose was similar in the basal state in the two groups (2.0±0.2 and 2.1±0.3 mg/kg/min) and was completely suppressed during insulin infusion in both cases.

Thus, the results of this study show that the acute intravenous administration of L-carnitine is effective in potentiating the stimulatory effect of insulin on the uptake of glucose by peripheral tissues in non-insulin-dependent diabetics. The improvement in glucose utilization achieved in these patients proved quantitatively similar to that previously documented in normal subjects (17%) [Ferrannini E. et al. (1988) Interaction of carnitine with insulin-stimulated glucose metabolism in man. Am. J. Physiol. 18, 946–952]. The effect of L-carnitine was independent of body weight and/or degree of insulin resistance.

2nd CLINICAL TRIAL

Oral Administration

L-carnitine was administered to a group of 24 patients with non-insulin-dependent diabetes (insulin-resistant). All patients were stabilized by treatment with oral hypoglycaemic agents.

They were thus admitted to the trial with what tended by and large to be constant serum glucose values. These values were systematically higher than those of healthy subjects. The treatment with oral hypoglycaemic agents was continued throughout the trial at routine doses for all patients. L-carnitine was administered in the form of an oral solution at doses of 2–3 g/day L-carnitine according to body weight.

The diet was kept constant throughout the trial.

The duration of L-carnitine treatment was 4 months for all patients. L-carnitine activity was measured on the basis of the following parameters: fasting and postprandial plasma glucose, urinary glucose, insulin and non-esterified fatty acids (NEFA). Observations were performed at time 0, i.e. before administration of L-carnitine, and thereafter at 30-day intervals (at 30, 60, 90 and 120 days of L-carnitine administration). Both fasting and postprandial plasma glucose levels diminished on average by 30% in 16 of the patients treated (⅔ of samples). Insulin and NEFA showed no significant changes. Urinary glucose, when present, disappeared or decreased. The oral L-carnitine trial thus confirms the data obtained in the acute study according to the euglycaemic insulin clamp model, where L-carnitine was administered i.v.

The trial confirms that L-carnitine administered orally at doses ranging from 2 to 3 g/day increases the peripheral utilization of glucose by reducing insulin resistance in-type-II diabetics.

Though the daily dose to be administered depends, utilizing sound professional judgement, on the patient's body weight, age and general condition, we found that it is generally advisable to administer from approximately 20 to approximately 50 mg of L-carnitine/kg b.w./day or an equivalent amount of an acyl-L-carnitine or one of its pharmacologically acceptable salts.

L-carnitine and the acyl-L-carnitines are formulated with the usual excipients used for the preparation of compositions suitable for oral or parenteral administration, which are well known to experts in pharmacy.

In view of the dose to be administered, a pharmaceutical composition particularly suitable for the above-mentioned therapeutic use will include, when given in the form of a unit dosage, 1000 mg of L-carnitine or an equivalent amount of an acyl-L-carnitine or one of its pharmacologically acceptable salts.

TABLE
CLINICAL CHARACTERISTICS OF PATIENTS

| Patients (No.) | Sex (M/F) | Age (yrs) | BMI (kg/m³) | FPI (μU/ml) | Duration of diabetes (yrs) | Therapy |
|---|---|---|---|---|---|---|
| 1 | M | 64 | 27 | 8 | 20 | OHA |
| 2 | M | 39 | 28 | 8 | 7 | OHA |
| 3 | F | 43 | 26 | 11 | 4 | OHA |
| 4 | F | 56 | 33 | 14 | 10 | OHA |
| 5 | M | 66 | 26 | 9 | 3 | OHA |
| 6 | M | 54 | 22 | 9 | 6 | I |
| 7 | M | 53 | 29 | 13 | 12 | I |
| 8 | M | 55 | 29 | 11 | 15 | OHA |
| 9 | M | 58 | 24 | 9 | 4 | OHA |
| Mean ± SE | | 54 ± 3 | 27 ± 1 | 9 ± 2 | 10 ± 1 | |

FPI = fasting plasma insulin; I = insulin; OHA = oral hypoglycaemic agent; BMI = body mass index

I claim:

1. A therapeutical method for enhancing peripheral glucose utilization in a non-insulin-dependent diabetic patient which comprises orally or parenterally administering to a patient in need thereof a composition consisting of 20–50 mg of L-carnitine/kg body weight/day or an equivalent amount of alkanoyl L-carnitine wherein the alkanoyl is a straight or branched-chain alkanoyl group having 2–6 carbon atoms or a pharmacologically acceptable salt thereof, and pharmaceutical excipient.

2. The method of claim 1, wherein the acyl L-carnitine is selected from the group consisting of acetyl, propionyl, butyryl, valeryl and isovaleryl L-carnitine.

3. The method of claim 1, wherein the pharmacologically acceptable salt is selected from the group consisting of chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

* * * * *